US010561700B2

(12) United States Patent
Wu et al.

(10) Patent No.: US 10,561,700 B2
(45) Date of Patent: *Feb. 18, 2020

(54) **USE OF OVERGROUND PART OF *HEDYCHIUM CORONARIUM* KOENIG IN REDUCING BLOOD GLUCOSE; EXTRACTS AND COMPOSITIONS OF OVERGROUND PART OF *HEDYCHIUM CORONARIUM* KOENIG AND THEIR USES**

(71) Applicant: Development Center for Biotechnology, Xizhi, Taipei County (TW)

(72) Inventors: Rey Yuh Wu, Xizhi (TW); Yu-Yuan Wu, Xizhi (TW); Lung-Yu Kuan, Xizhi (TW); Klim King, Xizhi (TW)

(73) Assignee: Development Center for Biotechnology, Xizhi, Taipei County (TW)

( * ) Notice: Subject to any disclaimer, the term of this patent is extended or adjusted under 35 U.S.C. 154(b) by 315 days.

This patent is subject to a terminal disclaimer.

(21) Appl. No.: 15/359,555

(22) Filed: Nov. 22, 2016

(65) Prior Publication Data

US 2017/0087201 A1  Mar. 30, 2017

Related U.S. Application Data

(63) Continuation of application No. 13/015,256, filed on Jan. 27, 2011, now abandoned, which is a continuation-in-part of application No. 12/701,997, filed on Feb. 8, 2010, now abandoned.

(51) Int. Cl.
*A61K 36/906* (2006.01)

(52) U.S. Cl.
CPC ........ *A61K 36/906* (2013.01); *A61K 2236/13* (2013.01); *A61K 2236/15* (2013.01); *A61K 2236/17* (2013.01); *A61K 2236/30* (2013.01); *A61K 2236/53* (2013.01)

(58) Field of Classification Search
None
See application file for complete search history.

(56) References Cited

U.S. PATENT DOCUMENTS

| 6,576,270 B2 | 6/2003 | Leko |
| 6,770,307 B2 | 8/2004 | Yoon et al. |
| 6,780,440 B2 | 8/2004 | Naguib |
| 7,482,030 B2 | 1/2009 | Mansilla |

FOREIGN PATENT DOCUMENTS

| CN | 101773247 A | 7/2010 |
| JP | 08053360 A | 2/1996 |
| TW | 200421984 | 11/2004 |
| WO | 92/09295 A1 | 6/1992 |
| WO | WO 2002/056859 A2 | 7/2002 |

OTHER PUBLICATIONS

Dhawan B. N. et al.; "Screening of Indian Plants for Biological Activity: Part VI*;" Indian Journal of Expertmental Biology, vol. 15, Mar. 1977, pp. 208-219.
Extended European Search Report issued for the European application corresponding to U.S. Appl. No. 12/701,997, which was attached to our Sep. 1, 2010 e-mail.
Bhandary M.J. et al.: "Medial ethnobotany of the Siddis of Uttara Kannada district, Karnataka, India," Journal of Ethnopharmacology, vol. 47 (Jan. 1, 1995), pp. 149-158.
"Histamine release inhibitor, for cosmetics and food-comprises plant extracts e.g. Jambosa vulgaris," WPI World Patent INF, Feb. 27, 1996 (abstract).
Database WPI Week 200146 Thomson Scientific, London, GB: AN 2001-426239, Apr. 25, 2001 (abstract).
Database WPI Week 200843 Thomson Scientific, London, GB: AN 2008-G72643, Dec. 26, 2007 (abstract).
Database WPI Week 199618 Thomson Scientific, London, GB: AN 1996-175673, Feb. 27, 1996 (abstract).
"Cosmetic material contg. at lest one vegetable extract(s)—used to prevent hot feeling after sunburn, rough skin, etc," Derwent, Dec. 22, 1986 (abstract).
Chen Zhi-hui, "Optimization of extraction process of hedychium coronarium essential oil by orthogonal design", China Condiment, Dec. 2004, No. 12, pp. 17-19 (English abstract only).
Chen Zhi-hui "Study on Essence Oils from Hedychium coronarium by Microwave Method," Lishizhen Medicine and Meteria Medica Research, vol. 16, issue 7, Jul. 20, 2005. (English Abstract).
He Er-yang "Study on Hedgchlum Coranagium Kocnlg's Edibility and its Pharmacological Experiments," Lishizhen Medicine and Meteria Medica Research, vol. 11, issue 12, Dec. 20, 2000. (English Abstract).
Liu Li-juan, "Progress in the Studies on Chemical Constituents of Hedychium," Journal of the Graduates Sun YAT-SEN University, vol. 23, issue 2, Feb. 28, 2002. (English Abstract).
Na Zhi "Chemical Constituents of the Volatile Oil from the Rhizome of Hedychium forrestii Diels," Journal of Tropical and Subtropical Botany, vol. 14, issue 5, pp. 417-420, Oct. 30, 2006. (English Abstract).
Peng Bing-xian, et al., "Determination of Chemical Constituents in Volatile Oil from Hedychium coronarium," Lishizhen Medicine and Meterial Medica Research, vol. 19, issue 6, Jun. 20, 2006. (English Abstract).

(Continued)

*Primary Examiner* — Terry A McKelvey
*Assistant Examiner* — Catheryne Chen
(74) *Attorney, Agent, or Firm* — McDonnell Boehnen Hulbert & Berghoff LLP (57) ABSTRACT

The present invention is related to the use of an overground part of *Hedychium coronarium* Koenig in lowering blood glucose, increasing insulin levels and treating and/or preventing diabetes without overly reducing blood glucose in a subject; i.e., not reducing blood glucose in a fasting subject. The present invention also relates to an extract and composition of the overground part of *Hedychium coronarium* Koenig and its use in lowering blood glucose, increasing insulin levels and treating and/or preventing diabetes.

10 Claims, 9 Drawing Sheets

(56) References Cited

OTHER PUBLICATIONS

Nakamura, et al., "Medicinal Flowers. XXIV.1. Chemical Structures and Hepatoprotective Effects of Constituents from Flowers of Hedychium Coronarium", Chem. Pharm. Bull., 2008, vol. 56, pp. 1704-1709.
Ribeiro Rosana de A., "Acute Diuretic Effects in Conscious Rats Produced by Some Medicinal Plants Used in the State of Sao Paulo Brasil," Journal of Ethnopharmacology, vol. 24, 1988, pp. 19-29. (English Abstract).
Chan, Eric, et al., "Phytochemistry and Pharmacology of Ornamental Gingers, *Hedychium coronarium* and *Alpinia purpurata* : A Review", J. Integr. Med., Nov. 2015, vol. 13(6), pp. 368-379, doi:10.1016/S2095-4964(15)60208-4.

USE OF OVERGROUND PART OF *HEDYCHIUM CORONARIUM* KOENIG IN REDUCING BLOOD GLUCOSE; EXTRACTS AND COMPOSITIONS OF OVERGROUND PART OF *HEDYCHIUM CORONARIUM* KOENIG AND THEIR USES

CROSS-REFERENCE TO RELATED APPLICATION

This application is a continuation application of U.S. patent application Ser. No. 13/015,256 filed Jan. 27, 2011 (abandoned), which is a continuation-in-part of U.S. patent application Ser. No. 12/701,997, filed Feb. 8, 2010 (abandoned), the disclosures of which are incorporated herein by reference in their entirety.

FIELD OF THE INVENTION

The present invention is related to the use of an herb in lowering blood glucose, increasing insulin levels and treating and/or preventing diabetes. Specifically, the invention provides the use of an overground part of *Hedychium coronarium* Koenig in lowering blood glucose, increasing insulin levels, and treating and/or preventing diabetes, and the extract and composition of the overground part of *Hedychium coronarium* Koenig and its use.

BACKGROUND OF THE INVENTION

Diabetes is a disease process resulting from multiple causative factors and is characterized by elevated levels of plasma glucose during the fasting state or after administration of glucose during an oral glucose tolerance test. Persistent or uncontrolled hyperglycemia is associated with increased and premature morbidity and mortality. Abnormal glucose homeostasis is often associated both directly and indirectly with alterations of the lipid, lipoprotein and apolipoprotein metabolism and other metabolic and hemodynamic diseases. There are two generally recognized forms of diabetes. Type 1 diabetes (also known as insulin-dependent diabetes mellitus or juvenile-onset diabetes) develops when the body's immune system destroys the pancreatic cells that produce the hormone insulin, which regulates blood glucose levels. Type 1 diabetes accounts for about 5 to 10 percent of all diagnosed cases of diabetes. Risk factors for type 1 diabetes include autoimmune, genetic, and environmental factors. Type 2 diabetes (also known as non-insulin-dependent diabetes mellitus or adult-onset diabetes), is a metabolic disorder resulting from the body's inability to either sufficiently produce insulin or properly use it. The onset of type 2 diabetes is usually characterized by insulin resistance, a disorder in which cells do not respond to insulin properly. As a result, an increasing amount of insulin is needed, and the pancreas gradually loses its ability to produce insulin. Type 2 diabetes is the most common form of the disease, accounting for 90-95 percent of diabetes. Type 2 diabetes is becoming an epidemic due to a greater prevalence of obesity and sedentary lifestyle. Gestational diabetes refers to a form of glucose intolerance that is diagnosed in pregnant women. During pregnancy, gestational diabetes requires treatment to normalize maternal blood glucose levels to avoid complications in the infant. A small percentage (about 5-10 percent) of women with gestational diabetes develop type 2 diabetes after pregnancy. Women who have had gestational diabetes also have a 20-50 percent chance of developing diabetes in the next 5-10 years.

Along with diet and exercise, treatment with insulin or hypoglycemia drugs is commonly employed to control diabetes. Treatment with these agents is successful in some cases, but the mortality index continues to rise. Insulin treatment provides symptomatic relief rather than a cure for non-insulin-dependent diabetes mellitus (NIDDM). Hypoglycemic agents such as sulfonylureas and biguanides (metformin) also lower blood glucose, but again only provide symptomatic relief. Sulfonylureas lower the blood glucose level by stimulating the release of insulin from pancreatic beta cells. These agents directly stimulate insulin release by closing adenosyl triphosphate (ATP)-sensitive potassium channels and depolarizing the cell membrane. The side effects of sulfonylureas include hypoglycemia, renal and hepatic disease, gastrointestinal disturbances, increased cardiovascular mortality, dermatological reactions, dizziness, drowsiness and headaches. Biguanides lower blood glucose levels by reducing intestinal glucose absorption and hepatic glucose; however, they do not stimulate insulin secretion. The major side effects of biguanidine are lactic acidosis and increased cardiovascular mortality. Alpha glucosidase inhibitors inhibit intestinal alpha glucosidases and consequently delay the digestion of sucrose and complex carbohydrates. The side effects of alpha glucosidase inhibitors include gastrointestinal side effects and hypoglycemia. Thiazolidinediones improve insulin resistance directly, enhancing the effects of circulating insulin by directly stimulating peripheral glucose uptake and inhibiting glucose production in the liver. However, thiazolidinediones are only effective in the presence of insulin and may cause red blood cell abnormalities and headache. Therefore, researchers have long been interested in medicinal plants as a possible source for the development of anti-diabetic agents.

U.S. Pat. No. 6,780,440 provides herbal compositions suitable for weight loss management and for treating diabetes and comprising *Ferula hermonis*, an extract thereof or a combination of *Ferula hermonis* and selected herbs, extracts thereof, and a mixture thereof suitable for weight loss management. U.S. Pat. No. 6,770,307 refers to an herbal medicinal composition for preventing or treating type II diabetes, which comprises extracts from *Pterocarpus marsupium, Morus alba, Orthosiphon aristatus, Opiophogon japonicus, Rosa rugosa, Commelina communis, Trichosanthis kirilowii* and *Anemarrhena asphodeloides*. U.S. Pat. No. 6,576,270 refers to the herbal composition against diabetes, which consists of *Centaurii umbellatum*, Gentianaceae (centaury plant), *Teraxacum officinale*, Asteraceae (dandelion root), *Juniperi communis* L, Cupresaceae (juniper berry), *Urticae dioica* L, Urticeae (nettle plant), *Urticae dioica* L, Urticaceae (nettle root), *Cichorium intybus* L, Cichoriaceae (chicory root), *Morus nigra* L, Moraceae, (mulberry leaf), *Achilleae millefolium* L, Asteraceae (yarrow flower), *Vaccinium myrtillus* L, Ericaceae (bilberry leaf), *Phaseolus vulgaris* L, Fabaceae (bean pods), *Valeriana officinalis* L, Valerlanaceae (Valerian root). U.S. Pat. No. 7,482,030 refers to a new composition comprising the herbs *Mulinum spinosum* and *Chamaemelum nobile* for treatment of diabetes.

Even though Dhawan B. N. et al. (Indian Journal of Expertmental Biology, Vol. 15, March 1977, pp. 208-219) discloses that an essential oil extracted from the rhizome of *Hedychium spicatum* Buch-Ham, an allied species of *Hedychium coronarium*, has been found to be hypoglycaemic, and Bhandary M. J. et al. (Journal of Ethnopharmacology, 47 (1995) 149-158) found that a mixture of the dried rhizome powder of *Hedychium coronarium* Koening with milk is traditionally used at some area in India to treat diabetes, as concluded by Bhandary M. J. et al. (1995), in order to discover the true potential of these medicines, pharmco-chemical studies are needed. Therefore, there is a continued need for novel herbal medicaments for blood glucose reduction and treatment and/or prevention of diabetes.

SUMMARY OF THE INVENTION

The invention provides a method for lowering blood glucose, increasing insulin levels and/or reducing insulin resistance by administering an effective amount of an overground part of *Hedychium coronarium* Koenig to a subject.

The invention also provides a method for treating and/or preventing diabetes by administering an effective amount of an overground part of *Hedychium coronarium* Koenig to a subject. Preferably, the diabetes is type I or type II.

The invention further provides a method for making an extract of an overground part of *Hedychium coronarium* Koenig, and the extract prepared thereby which can be used to lower blood glucose, increase insulin levels, reduce insulin resistance and prevent and/or treat diabetes.

The invention also provides a pharmaceutical composition containing an overground part of *Hedychium coronarium* or its extract mixed with suitable pharmaceutically acceptable excipients.

DETAILED DESCRIPTION OF THE INVENTION

The invention surprisingly found that the overground part of *Hedychium coronarium* Koenig can be used to increase plasma levels of insulin, lower blood glucose and treat and/or prevent diabetes. Unlike traditional sulfonylurea compounds, its action is glucose-dependent and consequently will not cause hypoglycemia, i.e., it will not reduce blood glucose in a fasting subject. On the basis of this discovery, the extract of an overground part of *Hedychium coronarium* Koenig can be used to promote the secretion of insulin and lower blood glucose, and thus act as an anti-diabetic agent.

An object of the invention is to provide a use of an overground part of *Hedychium coronarium* Koenig in the manufacture of a medicament for lowering blood glucose, increasing insulin levels and/or reducing insulin resistance. Alternatively, the invention provides a method for lowering blood glucose, increasing insulin levels and/or reducing insulin resistance comprising administering an effective amount of an overground part of *Hedychium coronarium* Koenig to a subject.

Another object of the invention is to provide a use of an overground part of *Hedychium coronarium* Koenig in the manufacture of a medicament for treating and/or preventing diabetes. Alternatively, the invention provides a method for treating and/or preventing diabetes, comprising administering an effective amount of an overground part of *Hedychium coronarium* Koenig to a subject.

A further object of the invention is to provide a method for making an extract of an overground part of *Hedychium coronarium* Koenig, and the extract prepared thereby which can be used to lower blood glucose, increase insulin levels, reduce insulin resistance and prevent and/or treat diabetes.

Another object of the invention is to provide a pharmaceutical composition comprising an overground part of *Hedychium coronarium* or its extract together with suitable pharmaceutically acceptable excipients. Unlike other medications, administration of the composition of the present invention will not overly reduce blood glucose in a subject; i.e., it will not reduce blood glucose in a fasting subject.

As used herein, an "anti-diabetic" or "hypoglycemic" compound or composition refers to an agent that lowers blood glucose levels. The hypoglycemic or anti-diabetic effect can be measured by a variety of methods including, but not limited to, measuring blood glucose levels and plasma levels of insulin.

As used herein, "extract" refers to a concentrated preparation of the essential constituents of the medicinal plant. Typically, an extract is prepared from a fresh plant or a dried and/or powdered plant sample. Optionally, the plant and the dried and/or powdered plant sample may be heated in a solution. The extract may be used in liquid form, or mixed with other liquid or solid medicinal herbal extracts. Alternatively, the medicinal herbal extract of the present invention may be obtained by further precipitating solid extracts from the liquid form. Typically, an extract is prepared by drying and subsequently cutting or grinding the dried material or vice versa. The extraction process may then be performed with the help of an appropriate solvent by means of maceration, percolation, repercolation, counter-current extraction, turbo-extraction, or by carbon-dioxide hypercritical (temperature/pressure) extraction. The solvent can be, but is not limited to, water, ethanol, an ethanol/water mixture, methanol, butanol, iso-butanol, acetone, hexane, petroleum ether, ethyl acetate, or other organic solvents. The extract may then be further evaporated and thus concentrated to yield a soft extract (extractum spissum), a dried extract and/or extracum siccum, by means of spray drying, vacuum oven drying, fluid-bed drying or freeze-drying.

As used herein, "treat," "treating," and "treatment" refer to the use of a compound, composition, therapeutically active agent, or drug in the diagnosis, cure, mitigation, treatment, or prevention of disease or other undesirable conditions.

*Hedychium coronarium*

As used herein, *Hedychium coronarium* Koenig, *Hedychium coronarium*, its synonyms *Gandasulium coronarium*, *Gandasulium lingulatum*, *Hedychium coronarium* var. maximum, *Hedychium lingulatum* and its common names butterfly lily, garland flower, white ginger, garland lily, and Sierra Leone Krio lili refer to the same plant, Amomun filiforme. *Hedychium coronarium* Koenig is a robust, attractive plant that will reach 6 feet when grown in containers. Its leaves are lance-shaped, sharp-pointed, 8-24 cm long and 2-5 cm wide and arranged in 2 neat ranks that run the length of the pseudostem. From midsummer through autumn, the stalks are topped with 6-12 cm long clusters of fragrant white flowers that look like butterflies. The flowers eventually give way to showy seed pods chock-full of bright red seeds. The plants are very robust, quickly growing beyond the capacity of their containers, and need to be divided yearly. Old stems should be removed after flowers have faded in order to promote new growth.

According to the invention, the overground part of the plant *Hedychium coronarium* Koenig can be used to lower blood glucose, increase insulin levels, reduce insulin resistance and treat and/or prevent diabetes. According to one embodiment of the invention, the overground part includes leaves and/or pseudostem of the plant. More preferably, the leaves and pseudostem of *Hedychium coronarium* are used in the invention.

Extract of an Overground Part of *Hedychium coronarium*

According to the invention, the extract of the overground part of *Hedychium coronarium* is prepared by extracting the part with a solvent at a ratio of about 1:1 to about 1:100 (w/v (g/ml)) (preferably about 1:5 to about 1:50 (w/v (g/ml)), more preferably about 1:10 to about 1:20 (w/v (g/ml)), and most preferably about 1:10 (w/v) (g/ml)). Preferably, the part is extracted using water, ethanol or a water/ethanol mixture. According to one embodiment of the invention, the extract can be prepared by washing the overground part of the plant, grinding and drying the plant sample, mixing the ground-dried plant sample with a solvent (such as water, ethanol or a mixture thereof) for extraction, filtrating the resulting extract solution, concentrating the extract solution (preferably under reduced pressure) and drying the resulting extract (preferably through freeze-drying). Preferably, the extraction is performed at an appropriate temperature depending on the solvent used for a suitable period. For example, extraction with ethanol is performed at a temperature of about 10° C. to about 45° C. (preferably about 20° C. to about 40° C. and more preferably about 25° C.) and extraction with water is performed at a temperature of about 50° C. to about 100° C. (preferably about 65° C. to about 95° C. and more preferably about 90° C.). Preferably, the extraction is performed for an appropriate duration depending on the solvent and temperature used. For example, extraction with ethanol at 25° C. is performed for more than 10 hours (preferably, about 16 hours), while extraction with water at 100° C. is performed for about 1 hour. According to another embodiment of the invention, the extraction can be performed more than one time.

In one embodiment, the invention provides a water extract of an overground part of *Hedychium coronarium*. Such a water extract is prepared by washing the overground part of the plant *Hedychium coronarium* (preferably, the leaves and pseudostem of *Hedychium coronarium*), grinding and drying (at about 60° C.) the plant sample to obtain a ground-dried plant sample, extracting the ground-dried plant sample with water at about 100° C. at a ratio of about 1:10 (w/v (g/ml)) for about 1 hour to obtain a crude product, filtrating and centrifuging the crude product to obtain a water extract, optionally re-extracting the remaining plant sample with water at about 100° C. at a ratio of about 1:10 (w/v (g/ml)) for about 1 hour to obtain a further crude product, filtrating and centrifuging the further crude product to obtain a further water extract, optionally combining the water extracts obtained from the previous two extractions to obtain a combined water extract, and concentrating the combined water extract to obtain a concentrated-combined water extract, and optionally preparing the concentrated-combined water extract in different dosages.

In another embodiment, the invention provides an ethanol extract of an overground part of Hedychium coronarium. Such an ethanol extract is prepared by washing the overground part of the plant Hedychium coronarium (preferably, the leaves and pseudostem of Hedychium coronarium), grinding and drying (at about 60° C.) the plant sample to obtain a ground-dried plant sample, extracting the ground-dried plant sample with 95% ethanol at a ratio of about 1:10 (w/v (g/ml)) for about 16 hours to obtain a crude product, filtrating and centrifuging the crude product to obtain an ethanol extract, optionally re-extracting the remaining plant sample with ethanol at a ratio of about 1:10 (w/v (g/ml)) to obtain a further crude product, filtrating and centrifuging the further crude product to obtain a further ethanol extract, optionally combining the ethanol extracts obtained from the previous two extractions to obtain a combined ethanol extract, and concentrating the combined ethanol extract under reduced pressure at an appropriate temperature (for example about 40° C.) to obtain a concentrated-combined ethanol extract, and optionally preparing the concentrated-combined ethanol extract in different dosages.

In a further embodiment, the invention provides a water-ethanol extract of an overground part of Hedychium coronarium. Such a water-ethanol extract is prepared by washing the overground part of the plant Hedychium coronarium (preferably, the leaves and pseudostem of Hedychium coronarium), grinding and drying (at about 60° C.) the plant sample to obtain a ground-dried plant sample, extracting the ground-dried plant sample with about 100° C. water at a ratio of about 1:10 (w/v (g/ml)) for about 1 hour to obtain a crude product, filtrating and centrifuging the crude product to obtain a water extract, optionally re-extracting the remaining plant sample with water at about 100° C. at a ratio of about 1:10 (w/v (g/ml)) for about 1 hour to obtain a further crude product, filtrating and centrifuging the further crude product to obtain a further water extract, optionally combining the water extracts obtained from the previous two extractions to obtain a combined water extract, diluting the combined water extract so that the v/w (ml/g) ratio of the diluted water extract to the ground-dried plant sample is about 1:1, adding ethanol to the diluted water extract so that the concentration of ethanol becomes about 70%, standing the ethanol solution for about 20 hours and then centrifuging and concentrating the resulting solution layer.

Pharmaceutical Composition Comprising an Overground Part of Hedychium coronarium or its Extract According to one aspect, the invention relates to pharmaceutical compositions comprising an overground part of Hedychium coronarium or its extract together with one or more suitable pharmaceutically acceptable excipients. Depending on the mode of administration, the pharmaceutical composition will preferably contain about 0.1 to about 100 wt % of the active ingredient, all percentages by weight being based on total composition.

In an embodiment of the invention, an overground part of Hedychium coronarium or its extract may be combined with one or more other anti-diabetic compounds and/or plant extracts. Preferably, an overground part of Hedychium coronarium or its extract may be used in combination with one or more Pterocarpus marsupium, Morus alba, Orthosiphon aristatus, Opiophogon japonicus, Anemarrhena asphodeloides, Trichosanthis kirilowii, Rosa rugosa, Commelina communis, and/or the extracts thereof to form an anti-diabetic composition. Any combination of these herbs may be used so long as the composition lowers blood glucose levels when administered to the patient.

Depending on the specific clinical status of the disease, the composition can be administered via any accepted systemic delivery system including but not limited to oral and parenteral routes such as intravenous, intramuscular, subcutaneous or percutaneous routes, vaginal, ocular or nasal routes in a solid, semi-solid or liquid dosage form, such as tablet, suppository, pill, capsule, powder, solution, suspension, cream, gel, implant, patch, pessary, aerosol, collyrium, and emulsion or the like, preferably in unit dosage forms suitable for easy administration of fixed dosages. The pharmaceutical compositions may include a conventional carrier or vehicle and may also include other medicinal agents, pharmaceutical agents, carriers, adjuvants, and so on. In the invention, the carrier for the herbal composition preferably includes a base of berries or fruit, a base of vegetable soup or bouillon, a soya-milk drink, or a nutritional supplement.

Utility or Treatment Method of an Overground Part of Hedychium coronarium, its Extract and a Pharmaceutical Composition Comprising the Same The inventors found that an overground part of Hedychium coronarium, its extract and a pharmaceutical composition comprising an overground part of Hedychium coronarium and/or its extract have a function in increasing the secretion of insulin and lowering blood glucose in a subject. In addition, the inventor found that the overground part of Hedychium coronarium, its extract and a pharmaceutical composition comprising the same will not overly reduce blood glucose in a subject; i.e., they will not reduce blood glucose in a fasting subject. Furthermore, an overground part of Hedychium coronarium, its extract and a pharmaceutical composition comprising the same can reduce insulin resistance. In view of the above, the overground part of Hedychium coronarium, its extract and a pharmaceutical composition comprising the same have an anti-diabetic function and thus can be used in the treatment or prevention of diabetes (including type I and type II diabetes). The invention provides an anti-diabetic agent that is highly tolerable by patients and exhibits few harmful side effects.

EXAMPLE

Figure 1:
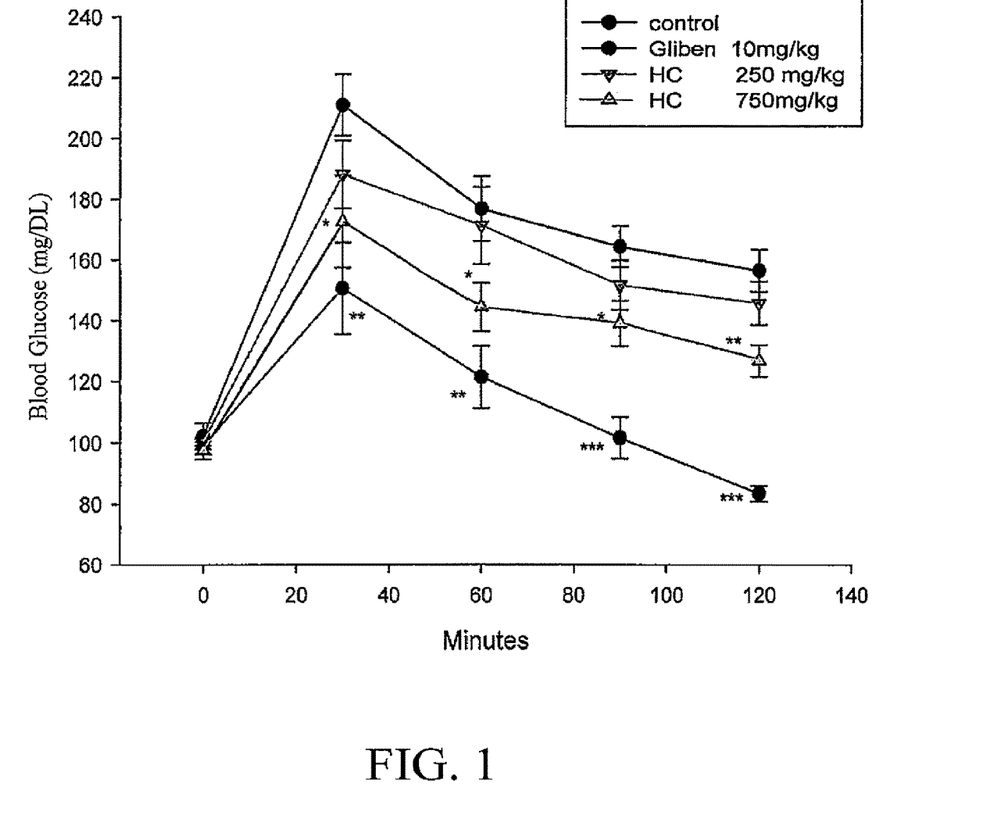
FIG. 1 illustrates the effect of ethanol extract of leaves and pseudostem of *Hedychium coronarium* Koenig in reducing blood glucose in normal rats. Control represents an oral administration of 10% Tween 20; Gliben 10 mg/kg represents an oral administration of 10 mg/kg glibenclamide; HC 250 mg/kg represents an oral administration of 250 mg/kg ethanol extract of leaves and pseudostem of *Hedychium coronarium*; and HC 750 mg/kg represents an oral administration of 750 mg/kg ethanol extract of leaves and pseudostem of *Hedychium coronarium*. The X axis represents the time intervals of blood sampling, and the Y axis represents the concentration of blood glucose.

Example 1 Glucose Tolerance Test of Ethanol Extract of Leaves and Pseudostem of Hedychium Coronarium in Normal Rats 26 Sprague-Dawley rats were divided into four groups: a placebo group (7 rats administered with 10% Tween 20), a positive control group (7 rats administered with glibenclamide), a 250 mg/kg HC group (6 rats administered with 250 mg/kg ethanol extract of the leaves and pseudostem of Hedychium coronarium) and a 750 mg/kg HC group (6 rats administered with 750 mg/kg ethanol extract of the leaves and pseudostem of Hedychium coronarium). The rats were fasted for 7 hours and were then administered with 250 mg/kg ethanol extract of the leaves and pseudostem of Hedychium coronarium (250 mg/kg HC group), 750 mg/Kg ethanol extract of the leaves and pseudostem of Hedychium coronarium (750 mg/kg HC group), 10 mg/kg glibenclamide (positive control group) and 10% Tween 20 (placebo group). After 30 minutes, each rat received a total of 5 g/kg of glucose (glucose was administrated both orally (2.5 g/kg) and subcutaneously (2.5 g/kg)). Blood samples were drawn at intervals of 0 minutes, 30 minutes, 60 minutes, 90 minutes and 120 minutes for the measurement of glucose (mg/DL). The results are shown in the table below and FIG. 1:

| | Concentration of blood glucose (mg/dl) | | | | |
|---|---|---|---|---|---|
| Group | 0 min | 30 mins | 60 mins | 90 mins | 120 mins |
| Placebo group | 102.1 +/− 4.2 | 211.1 +/− 10.2 | 177 +/− 10.7 | 164.6 +/− 6.7 | 156.9 +/− 7.0 |
| Glibenclamide group | 99 +/− 2.7 | 150.7 +/− 15.2** | 121.4 +/− 10.2** | 101.6 +/− 6.7** | 83.4 +/− 2.5*** |
| 250 mg/kg HC group | 100.2 +/− 1.3 | 188.2 +/− 11.1 | 171.5 +/− 12.6 | 151.8 +/− 8.1 | 146 +/− 7.2 |
| 750 mg/kg HC group | 97.5 +/− 2.8 | 172.7 +/− 15.1* | 144.5 +/− 8.0* | 139.2 +/− 7.5* | 127 +/− 5.2** |

The data is expressed with mean +/− standard error (SEM). P values are calculated by t-test of Sigma Statistical Software wherein $p < 0.05$ is considered significant and marked with *; $p < 0.01$ is considered highly significant and marked with ; and $p \leq 0.001$ is considered very highly significant and marked with *.

The results show that, compared with the control group, the 750 mg/kg HC group had significantly reduced blood glucose levels at intervals of 30, 60 and 90 minutes after administering glucose. The 750 mg/kg HC group had highly significantly reduced blood glucose levels 120 minutes after administering glucose.

Example 2 Glucose Tolerance Test of Ethanol Extract of Leaves and Pseudostem of *Hedychium Coronarium* in Mice with Type II Diabetes (Short-Term Postprandial Blood Glucose)

Figure 2:
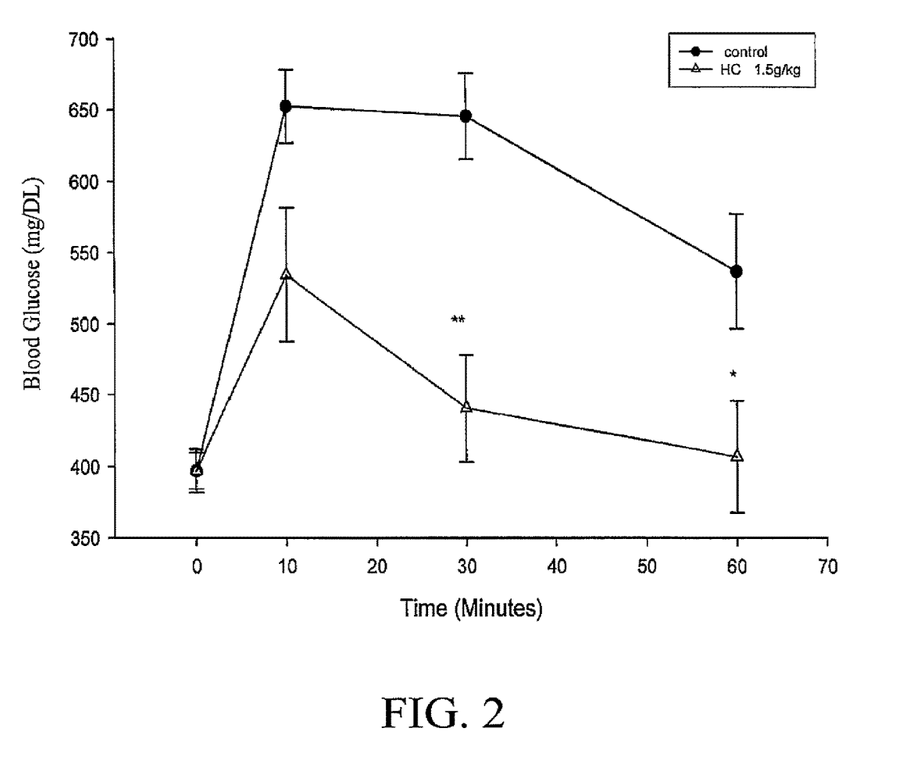
FIG. 2 illustrates through the glucose tolerance test the effect of ethanol extract of leaves and pseudostem of *Hedychium coronarium* Koenig in reducing blood glucose in $db^+/db^+$ mice with type II diabetes. Control represents an oral administration of 10% Tween 20; and HC 1.5 g/kg represents an oral administration of 1.5 g/kg ethanol extract of leaves and pseudostem of *Hedychium coronarium*. The X axis represents the time intervals of blood sampling, and the Y axis represents the concentration of blood glucose. P values are calculated by t-test of Sigma Statistical Software wherein $p<0.05$ is considered significant and marked with *; $p<0.01$ is considered highly significant and marked with ; and $p\leq0.001$ is considered very highly significant and marked with *.

Twelve mice with type II diabetes ($db^+/db^+$ mice) were fasted for 12 hours and then allowed to feed freely for two hours. Subsequently, the 6 mice of the control group were orally administered with 10% Tween 20 and the 6 mice of 1.5 g/kg HC group were orally administered with 1.5 g/kg ethanol extract of the leaves and pseudostem of *Hedychium coronarium*. Blood was drawn at intervals of 0 minutes, 10 minutes, 30 minutes and 60 minutes after administering the ingredients for measurement of glucose (mg/DL). The results are shown in the table below and FIG. 2:

| | Concentration of blood glucose (mg/DL) | | | |
|---|---|---|---|---|
| Group | 0 min | 10 mins | 30 mins | 60 mins |
| Control group; N = 6 | 397.0 ± 12.6 | 652.2 ± 25.5 | 645 ± 29.8 | 536.3 ± 40.3 |
| HC group; N = 6 | 396.8 ± 15.1 | 534.3 ± 47.0 | 440.2 ± 37.2** | 406.5 ± 38.8* |

The data is expressed with mean +/− standard error (SEM). P values are calculated by t-test of Sigma Statistical Software wherein $p < 0.05$ is considered significant and marked with *; $p < 0.01$ is considered highly significant and marked with ; and $p \leq 0.001$ is considered very highly significant and marked with *.

The results show that compared with the control group, the 1.5 g/kg HC group had highly significantly and significantly reduced blood glucose levels 30 and 60 minutes after administering glucose, respectively.

Figure 3:
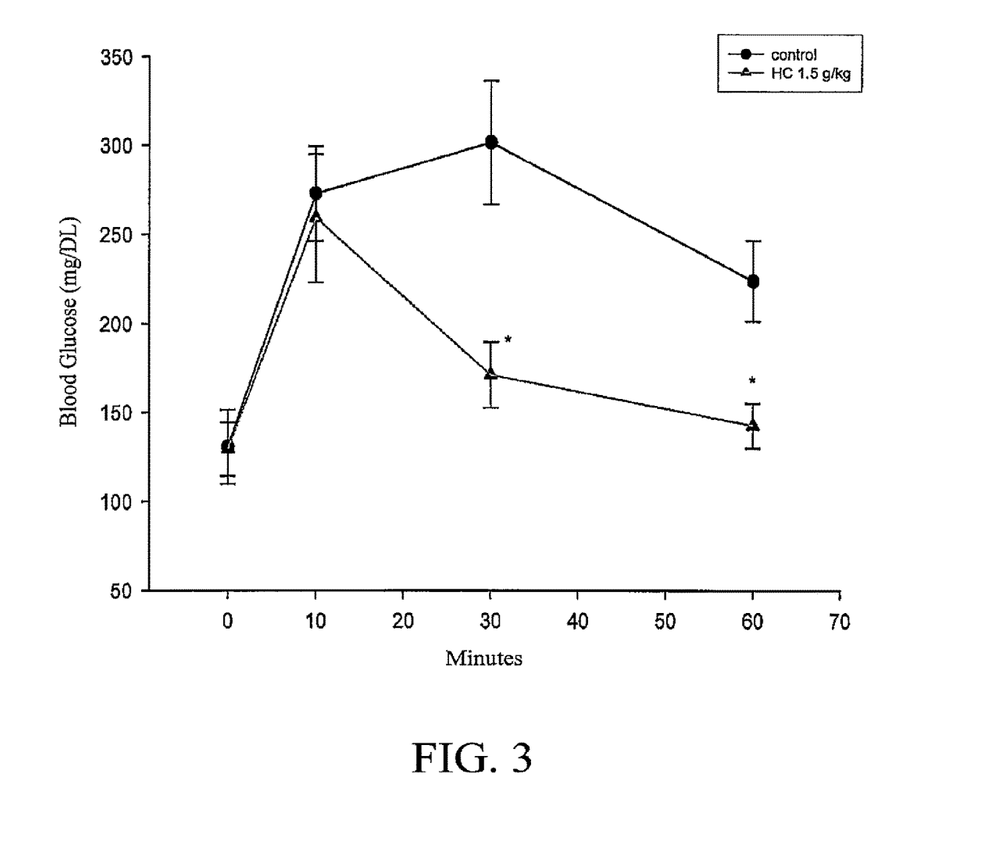
FIG. 3 illustrates through the intraperitoneal glucose tolerance test the effect of ethanol extract of leaves and pseudostem of *Hedychium coronarium* Koenig in reducing blood glucose in normal $db^-/db^-$ mice. Control represents an oral administration of 10% Tween 20; and HC 1.5 g/kg represents an oral administration of 1.5 g/kg ethanol extract of leaves and pseudostem of *Hedychium coronarium*. The X axis represents the time intervals of blood sampling, and the Y axis represents the concentration of blood glucose.

Example 3 Intraperitoneal Glucose Tolerance Test of Ethanol Extract of Leaves and Pseudostem of *Hedychium Coronarium* in Normal Mice Eight mice ($db^-/db^-$ mice) were divided into two groups: a control group (4 mice administered with 10% Tween 20) and a 1.5 g/kg HC group (4 mice administered with 1.5 g/kg ethanol extract of the leaves and pseudostem of *Hedychium coronarium*). The mice were fasted for 14 hours and then allowed to feed freely for two hours. Subsequently, they were orally administered with 10% Tween 20 for the control group and 1.5 g/kg ethanol extract of the leaves and pseudostem of *Hedychium coronarium* for the 1.5 g/kg HC group. After 30 minutes, each mouse was intraperitoneally administered with 1.5 g/kg glucose. Blood was drawn at intervals of 0 minutes, 10 minutes, 30 minutes and 60 minutes for measurement of glucose (mg/DL). The results are shown in the table below and FIG. 3:

| Concentration of blood glucose (mg/dl) | | | | |
|---|---|---|---|---|
| Group | 0 min | 10 mins | 30 mins | 60 mins |
| Control group | 130.8 +/− 20.7 | 273 +/− 26.5 | 301.8 +/− 34.8 | 224.3 +/− 22.6 |
| 1.5 g/kg HC group | 129.5 +/− 14.9 | 259.3 +/− 35.9 | 171.3 +/− 18.6* | 142.8 +/− 12.7* |

The data is expressed with mean +/− standard error (SEM). P values are calculated by t-test of Sigma Statistical Software wherein $p < 0.05$ is considered significant and marked with *; $p < 0.01$ is considered highly significant and marked with ; and $p \leq 0.001$ is considered very highly significant and marked with *.

The results show that compared with the control group, the 1.5 g/kg HC group had significantly reduced blood glucose levels 30 and 60 minutes after administering glucose. This demonstrates that blood glucose in normal mice can be significantly reduced.

Figure 4:
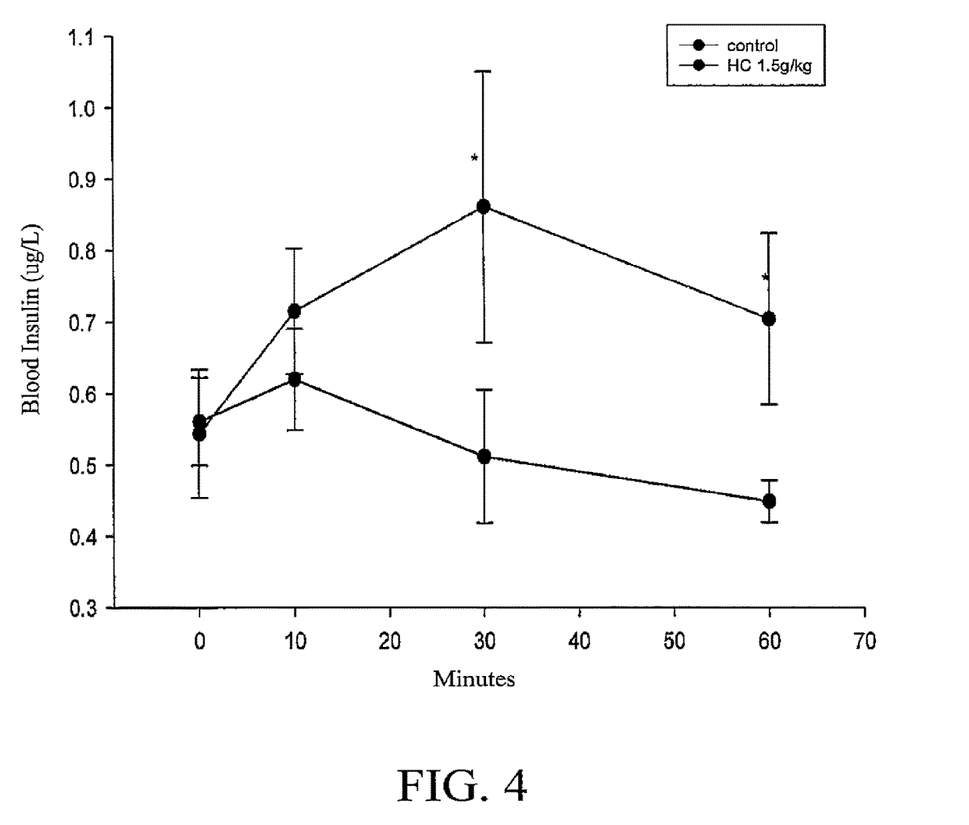
FIG. 4 illustrates through the intraperitoneal glucose tolerance test the effect of ethanol extract of leaves and pseudostem of *Hedychium coronarium* Koenig in promoting insulin secretion in normal $db^-/db^-$ mice. Control represents an oral administration of 10% Tween 20; and HC 1.5 g/kg represents an oral administration of 1.5 g/kg ethanol extract of leaves and pseudostem of *Hedychium coronarium*. The X axis represents the time intervals of blood sampling, and the Y axis represents the concentration of blood insulin.

Example 4 Insulin Increasing Test of Ethanol Extract of Leaves and Pseudostem of *Hedychium Coronarium* in Normal Mice The test mice and procedures were the same as those in Example 3. Blood was drawn at intervals of 0 minutes, 10 minutes, 30 minutes and 60 minutes for measurement of insulin (ug/L). The results are shown in the table below and FIG. 4:

| Concentration of Insulin (ug/L) | | | | |
|---|---|---|---|---|
| Group | 0 min | 10 mins | 30 mins | 60 mins |
| Control group | 0.56 +/− 0.04 | 0.62 +/− 0.05 | 0.51 +/− 0.07 | 0.45 +/− 0.02 |
| 1.5 g/kg HC group | 0.54 +/− 0.06 | 0.71 +/− 0.06 | 0.86 +/− 0.13* | 0.70 +/− 0.08* |

The data is expressed with mean +/− standard error (SEM). P values are calculated by t-test of Sigma Statistical Software wherein $p < 0.05$ is considered significant and marked with *; $p < 0.01$ is considered highly significant and marked with ; and $p \leq 0.001$ is considered very highly significant and marked with *.

The results show that compared with the control group, the 1.5 g/kg HC group had significantly increased insulin concentrations 30 and 60 minutes after administering glucose. This demonstrates that the ethanol extract of the leaves and pseudostem of *Hedychium coronarium* significantly promotes secretion of insulin.

Figure 5:
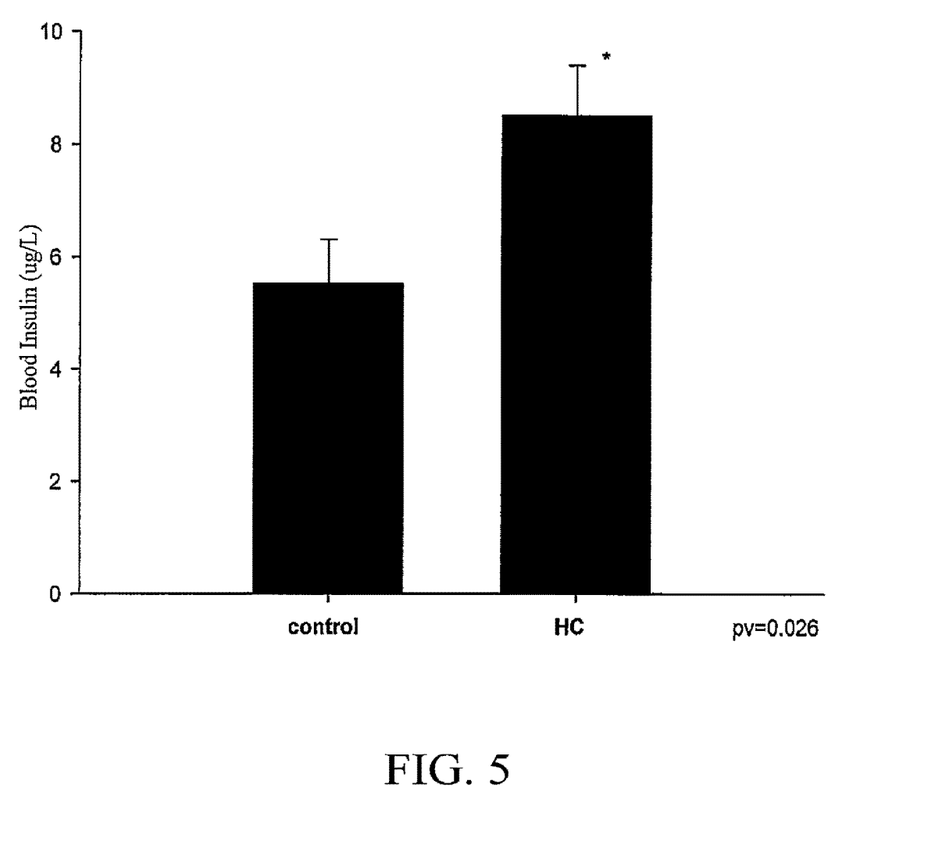
FIG. 5 illustrates through the glucose tolerance test the effect of ethanol extract of leaves and pseudostem of *Hedychium coronarium* Koenig in promoting insulin secretion in $db^+/db^+$ mice with type II diabetes. Control represents an oral administration of 10% Tween 20; and HC represents an oral administration of 1.5 g/kg ethanol extract of leaves and pseudostem of *Hedychium coronarium*. The X axis represents the time intervals of blood sampling, and the Y axis represents the concentration of blood insulin.

Example 5 Insulin Increasing Test of Ethanol Extract of Leaves and Pseudostem of *Hedychium Coronarium* in Mice with Type II Diabetes The test mice and procedures were the same as those in Example 2. Blood was drawn at 60 minutes for measurement of insulin (ug/L) and the results are shown in FIG. 5. The concentrations of insulin in the 1.5 g/kg HC group and control groups were 8.51+/−0.88 μg/L and 5.51+/−0.79 μg/L. These results show that the ethanol extract of the leaves and pseudostem of *Hedychium coronarium* significantly promotes the secretion of insulin in mice with type II diabetes.

Figure 6:
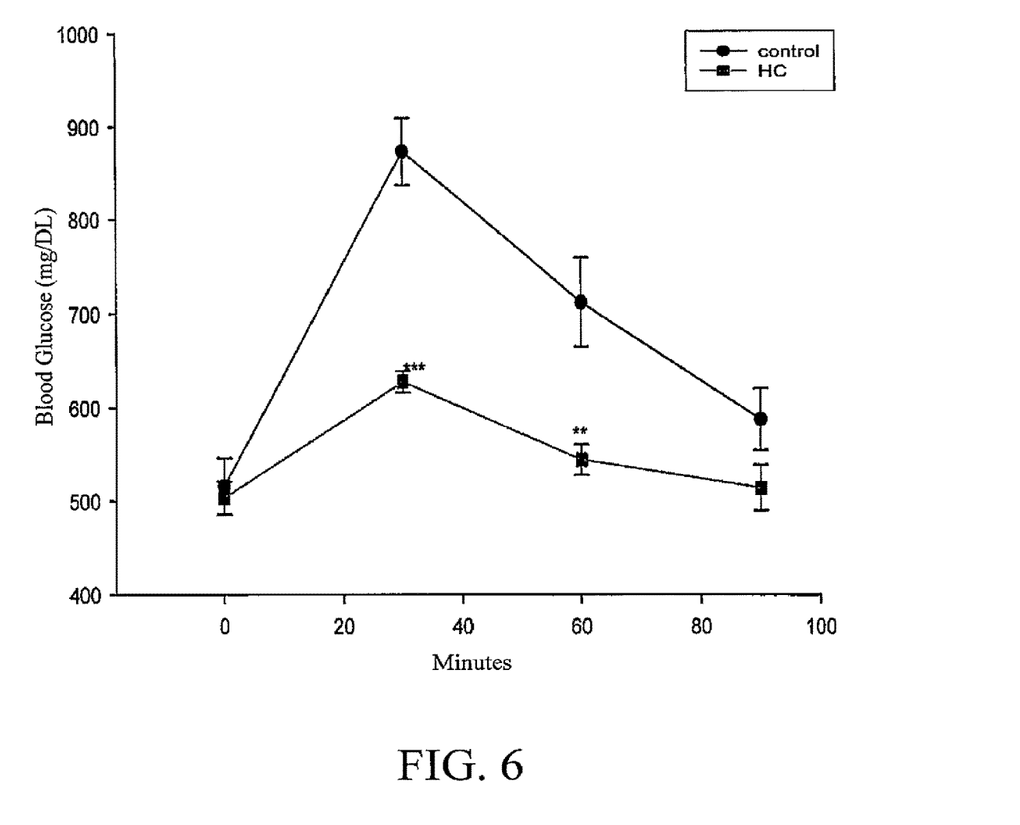
FIG. 6 illustrates through the glucose tolerance test the effect of ethanol extract of leaves and pseudostem of *Hedychium coronarium* Koenig in reducing blood glucose in rats with type I diabetes. Control represents an oral administration of 10% Tween 20; and a subcutaneous administration of normal saline, and HC represents an oral administration of 1 g/kg ethanol extract of leaves and pseudostem of *Hedychium coronarium*. The X axis represents the time intervals of blood sampling, and the Y axis represents the concentration of blood glucose.

Example 6 Glucose Tolerance Test of Leaves and Pseudostem of Ethanol Extract of *Hedychium Coronarium* in Rats with Type I Diabetes Twelve Sprague-Dawley rats with type I diabetes were divided into two groups: a control group (6 rats administered with 10% Tween 20) and a 1 g/kg HC group (6 rats administered with 1 g/kg ethanol extract of the leaves and pseudostem of *Hedychium coronarium*). The rats were fasted for 4 hours and then were orally administered with 10% Tween 20 for the control group and 1 g/Kg ethanol extract of the leaves and pseudostem of *Hedychium coronarium* for the 1 g/kg HC group. After 30 minutes, each rat was administered with 2.5 g/kg glucose. Blood samples were drawn at intervals of 0 minutes, 30 minutes, 60 minutes, and 90 minutes for the measurement of glucose (mg/dl). The results are shown in the table below and FIG. 6:

| Concentration of blood glucose (mg/dl) | | | | |
|---|---|---|---|---|
| Group | 0 min | 30 mins | 60 mins | 90 mins |
| Control group | 515.7 +/− 30.6 | 873 +/− 36.2 | 711.7 +/− 47.0 | 587.3 +/− 33.2 |
| 1 g/kg HC group | 503.5 +/− 17.8 | 627.8 +/− 11.3*** | 544 +/− 16.5** | 513.8 +/− 24.4 |

The data is expressed with mean +/− standard error (SEM). P values are calculated by t-test of Sigma Statistical Software wherein $p < 0.05$ is considered significant and marked with *; $p < 0.01$ is considered highly significant and marked with ; and $p \leq 0.001$ is considered very highly significant and marked with *.

The results show that compared with the control group, 1 g/kg ethanol extract of the leaves and pseudostem of *Hedychium coronarium* significantly reduces blood glucose 30 and 60 minutes after administering glucose. This shows that the ethanol extract of the leaves and pseudostem of *Hedychium coronarium* has an advantageous effect in reducing blood glucose in type I diabetes rats.

Figure 7:
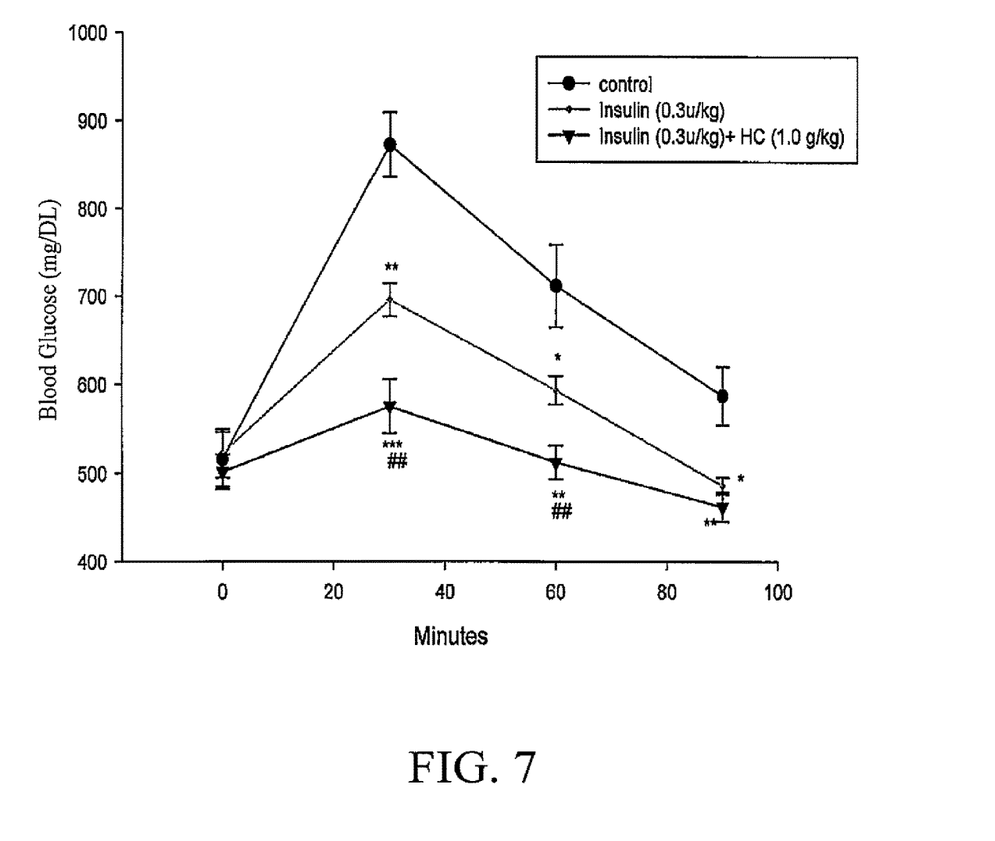
FIG. 7 illustrates through the glucose tolerance test the effect of ethanol extract of leaves and pseudostem of *Hedychium coronarium* Koenig in insulin resistance in rats with type I diabetes. Control represents an oral administration of 10% Tween 20 and a subcutaneous administration of normal saline; insulin (0.3 U/kg) represents an oral administration of 10% Tween 20 and a subcutaneous administration of 0.3 U/kg insulin; and insulin (0.3 U/kg)+HC (1.0 g/kg) represents an oral administration of 1 g/kg ethanol extract of leaves and pseudostem of *Hedychium coronarium* and a subcutaneous administration of 0.3 U/kg insulin. The X axis represents the time intervals of blood sampling, and the Y axis represents the concentration of blood glucose.

Example 7 Insulin Resistance Test of Ethanol Extract of Leaves and Pseudostem of *Hedychium Coronarium* in Rats with Type I Diabetes Eighteen Sprague-Dawley rats with type I diabetes were divided into three groups: a control group (6 rats administered with 10% Tween 20), an insulin group (6 rats subcutaneously administered with 0.3 U/kg insulin) and an insulin+HC group (6 rats subcutaneously administered with 0.3 U/kg insulin and orally administered with 1.0 g/kg of ethanol extract of the leaves and pseudostem of *Hedychium coronarium*). The rats were fasted for 4 hours and then were administered with 10% Tween 20 for the control group, 0.3 U/kg insulin for the insulin group and 0.3 U/kg insulin plus 1.0 g/Kg of ethanol extract of the leaves and pseudostem of *Hedychium coronarium* for the insulin+HC group. After 2.5 g/kg glucose was administered, blood was drawn at 30-minute intervals for measurement of glucose (mg/dl). The results are shown in the table below and FIG. 7:

| | Concentration of blood glucose (mg/dl) | | | |
|---|---|---|---|---|
| Group | 0 min | 30 mins | 60 mins | 90 mins |
| Control group | 515.7 +/− 30.6 | 873 +/− 36.2 | 711.7 +/− 47.0 | 587.3 +/− 33.2 |
| Insulin group | 522.5 +/− 27.1 | 695.8 +/− 18.7** | 593.3 +/− 16.2* | 486.2 +/− 9.6* |
| Insulin + HC group | 501.7 +/− 19.3 | 575.2 +/− 30.5*** ## | 512.3 +/− 19.2** ## | 462.3 +/− 16.9** |

The data is expressed with mean +/− standard error (SEM). P values are calculated by t-test of Sigma Statistical Software wherein $p < 0.05$ is considered significant and marked with * or #; $p < 0.01$ is considered highly significant and marked with  or ##; and $p \leq 0.001$ is considered very highly significant and marked with * (* represents the comparison between the insulin group or the insulin + HC group and the control group; # represents the comparison between the insulin group and the insulin + HC group).

As shown in the table, compared with the control group, the insulin group has a highly significant effect in reducing blood glucose levels 30 minutes after glucose is administered and has a significant effect in reducing blood glucose levels 60 and 90 minutes after glucose is administered. In addition, compared with the insulin group, the insulin+HC group has a significant effect in reducing blood glucose levels 30 and 60 minutes after glucose is administered.

Figure 8:
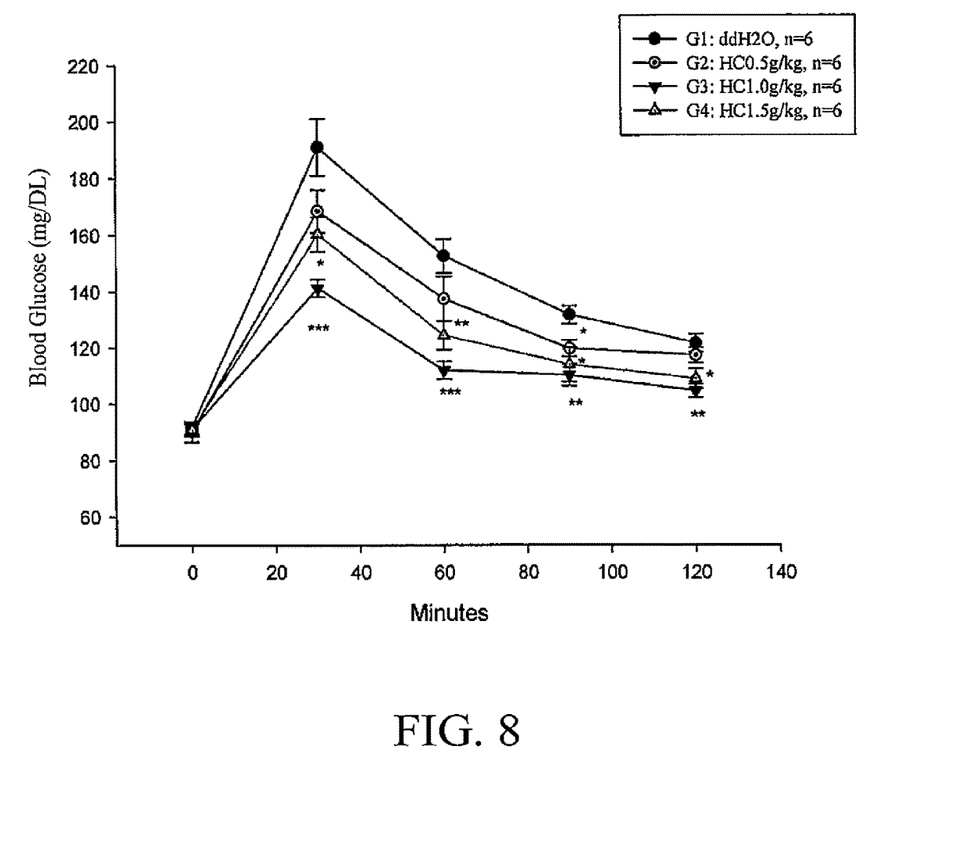
FIG. 8 illustrates through the glucose tolerance test the effect of water extract of the leaves and pseudostem of *Hedychium coronarium* Koenig in reducing blood glucose in normal rats. $ddH_2O$ represents an oral administration of $H_2O$; HC 0.5 g/kg represents an oral administration of 0.5 g/kg water extract of the leaves and pseudostem of *Hedychium coronarium* Koenig; HC 1.0 g/kg represents an oral administration of 1.0 g/kg water extract of the leaves and pseudostem of of *Hedychium coronarium*; and HC 1.5 g/kg represents an oral administration of 1.5 g/kg water extract of the leaves and pseudostem of *Hedychium coronarium*. The X axis represents the time intervals of blood sampling, and the Y axis represents the concentration of blood glucose.

Example 8 Glucose Tolerance Test of Water Extract of Leaves and Pseudostem of *Hedychium Coronarium* in Normal Rats The test rats and procedures were the same as those in Example 1. However, in this case, 24 Sprague-Dawley rats were used and divided into four groups: a placebo group (6 rats administered with water), a 0.5 g/kg HC group (6 rats administered with 0.5 g/kg water extract of the leaves and pseudostem of *Hedychium coronarium*), a 1 g/kg HC group (6 rats administered with 1 g/kg water extract of the leaves and pseudostem of *Hedychium coronarium*) and a 1.5 g/kg HC group (6 rats administered with 1.5 g/kg water extract of the leaves and pseudostem of *Hedychium coronarium*). After 30 minutes, each rat received a total of 5 g/kg of glucose (glucose was administrated both orally (2.5 g/kg) and subcutaneously (2.5 g/kg)). Blood was drawn at 30-minute intervals for measurement of glucose (mg/dl). The results are shown in the table below and FIG. 8:

| | Concentration of blood glucose (mg/dl) | | | | |
|---|---|---|---|---|---|
| Group | 0 min | 30 mins | 60 mins | 90 mins | 120 mins |
| Placebo group | 91.7 +/− 2.2 | 190.8 +/− 9.9 | 152.5 +/− 6.0 | 131.7 +/− 3.2 | 121.5 +/− 3.1 |
| 0.5 g/kg HC group | 90.2 +/− 3.5 | 168.3 +/− 7.4 | 137.3 +/− 7.9 | 119.7 +/− 7.4* | 117.2 +/− 2.7 |
| 1 g/kg HC group | 91.0 +/− 2.0 | 141.2 +/− 3.0*** | 111.8 +/− 3.1*** | 110.2 +/− 3.9** | 104.5 +/− 2.4** |
| 1.5 g/kg HC group | 90.8 +/− 2.3 | 160.2 +/− 6.1* | 124.3 +/− 5.2** | 114 +/− 6.1* | 108.8 +/− 3.6* |

The data is expressed with mean +/− standard error (SEM). P values are calculated by t-test of Sigma Statistical Software wherein $p < 0.05$ is considered significant and marked with *; $p < 0.01$ is considered highly significant and marked with ; and $p \leq 0.001$ is considered very highly significant and marked with *.

The results show that compared with the control group, 1 g/kg water extract of the leaves and pseudostem of *Hedychium coronarium* has a highly significant effect in reducing blood glucose 30 and 60 minutes after glucose is administered and has a very highly significant effect in reducing blood glucose 90 and 120 minutes after glucose is administered.

Figure 9:
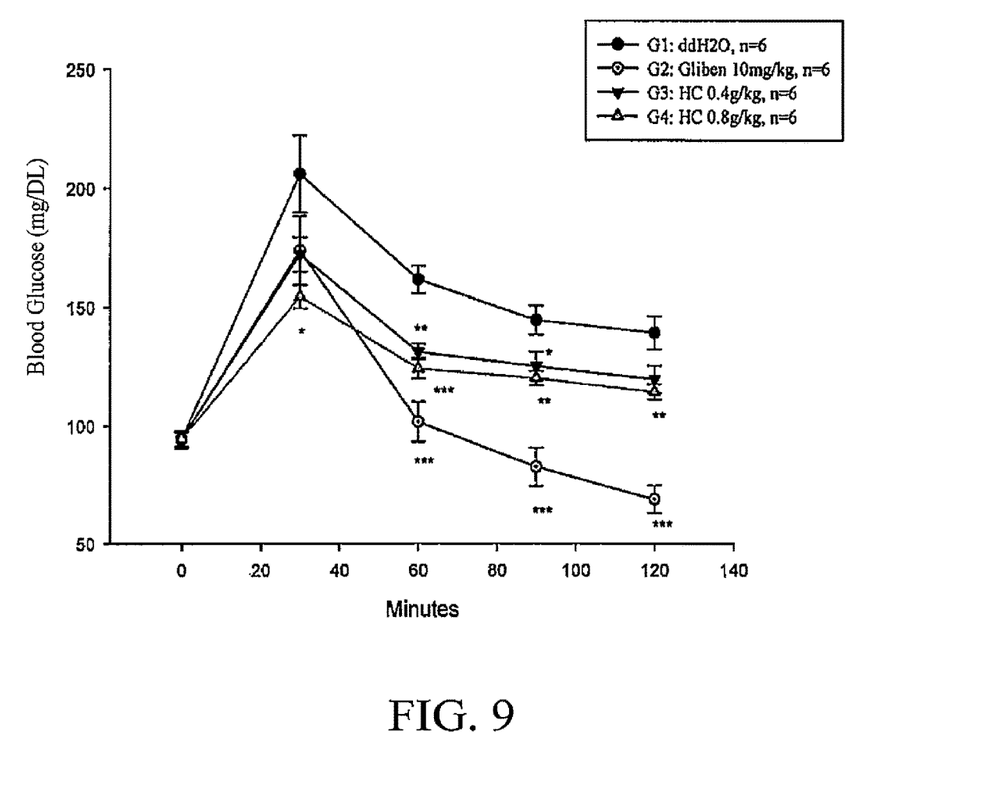
FIG. 9 illustrates through the glucose tolerance test the effect of water-ethanol extract of the leaves and pseudostem of *Hedychium coronarium* Koenig in reducing blood glucose in normal rats. $ddH_2O$ represents an oral administration of $H_2O$; Gliben 10 mg/kg represents an oral administration of 10 mg/kg glibenclamide; HC 0.4 g/kg represents an oral administration of 0.4 g/kg water-ethanol extract of the leaves and pseudostem of *Hedychium coronarium*; and HC 0.8 g/kg represents an oral administration of 0.8 g/kg water-ethanol extract of the leaves and pseudostem of *Hedychium coronarium*. The X axis represents the time intervals of blood sampling, and the Y axis represents the concentration of blood glucose.

Example 9 Glucose Tolerance Test of Water-Ethanol Extract of Leaves and Pseudostem of *Hedychium Coronarium* in Normal Rats The test rats and procedure were the same as those in Example 1. However, in this case, 24 Sprague-Dawley rats were used and divided into four groups: a placebo group (6 rats administered with water), a positive control group (6 rats administered with 10 mg/kg glibenclamide), a 0.4 g/kg HC group (6 rats administered with 0.4 g/kg water-ethanol extract of the leaves and pseudostem of *Hedychium coronarium*) and a 0.8 g/kg HC group (6 rats administered with 0.8 g/kg water-ethanol extract of the leaves and pseudostem of *Hedychium coronarium*). After 30 minutes, each rat received a total of 5 g/kg of glucose (glucose was administrated both orally (2.5 g/kg) and subcutaneously (2.5 g/kg)). Blood was drawn at 30-minute intervals for the measurement of glucose (mg/dl). The results are shown in the table below and FIG. 9:

| | Concentration of blood glucose (mg/dl) | | | | |
|---|---|---|---|---|---|
| Group | 0 min | 30 mins | 60 mins | 90 mins | 120 mins |
| Placebo group | 94.3 +/− 2.8 | 206 +/− 16.3 | 161.7 +/− 5.8 | 144.7 +/− 6.1 | 139.3 +/− 6.9 |
| glibenclamide group | 94.3 +/− 3.8 | 173.8 +/− 14.5*** | 101.8 +/− 8.4*** | 82.7 +/− 8.1*** | 68.8 +/− 5.9*** |
| 0.4 g/kg HC group | 94.3 +/− 3.1 | 172.2 +/− 7.3 | 131.3 +/− 3.4** | 125.3 +/− 6.0* | 119.8 +/− 5.8 |
| 0.8 g/kg HC group | 94.5 +/− 3.1 | 154.5 +/− 4.9* | 124.3 +/− 4.2*** | 120.3 +/− 3.0* | 114.5 +/− 3.3** |

The data is expressed with mean +/− standard error (SEM). P values are calculated by t-test of Sigma Statistical Software wherein $p < 0.05$ is considered significant and marked with *; $p < 0.01$ is considered highly significant and marked with ; and $p \leq 0.001$ is considered very highly significant and marked with *.

The results show that compared with the control group, 0.8 g/kg water-ethanol extract of the leaves and pseudostem of *Hedychium coronarium* has a significant effect in reducing blood glucose 30 minutes after glucose is administered, a very highly significant effect in reducing blood glucose 60 minutes after administering glucose and a highly significant effect in reducing blood glucose 90 and 120 minutes after glucose is administered.

Example 10 Glucose Tolerance Test of Water Extract of Rhizome of *Hedychium Coronarium* in Normal Rats The test rats and procedures were the same as those in Example 1. However, in this case, 24 Sprague-Dawley rats were used and divided into four groups: a placebo group (6 rats administered with water), a 0.5 g/kg HC group (6 rats administered with 0.5 g/kg water extract of the rhizome of *Hedychium coronarium*), a 1 g/kg HC group (6 rats administered with 1 g/kg water extract of the rhizome of *Hedychium coronarium*) and a 1.5 g/kg HC group (6 rats administered with 1.5 g/kg water extract of the rhizome of *Hedychium coronarium*). After 30 minutes, each rat received a total of 5 g/kg of glucose (glucose was administrated both orally (2.5 g/kg) and subcutaneously (2.5 g/kg)). Blood was drawn at 30-minute intervals for measurement of glucose (mg/dl). The results are shown in the table below.

| | Concentration of blood glucose (mg/dl) | | | | |
|---|---|---|---|---|---|
| Group | 0 min | 30 mins | 60 mins | 90 mins | 120 mins |
| Placebo group | 92.3 +/− 5.7 | 242.3 +/− 13.1 | 160.7 +/− 5.4 | 146.2 +/− 6.7 | 125.8 +/− 3.8 |
| 0.5 g/kg HC group | 90.2 +/− 4.0 | 246.3 +/− 17.1 | 151.7 +/− 2.9 | 135.3 +/− 3.9 | 126 +/− 5.2 |
| 1 g/kg HC group | 89.2 +/− 3.7 | 233.5 +/− 18.8 | 159.3 +/− 13.8 | 140 +/− 8.1 | 124.2 +/− 7.9 |
| 1.5 g/kg HC group | 89.5 +/− 3.3 | 218.8 +/− 10.9 | 152.7 +/− 5.9 | 146 +/− 5.0 | 129.7 +/− 3.9 |

The data is expressed with mean +/− standard error (SEM). P values are calculated by t-test of Sigma Statistical Software wherein $p < 0.05$ is considered significant and marked with *; $p < 0.01$ is considered highly significant and marked with ; and $p \leq 0.001$ is considered very highly significant and marked with *. The results show that compared with the control group, the groups administered with the water extracts of the rhizome of *Hedychium coronarium* showed no difference in the concentrations of blood glucose at all time points after glucose was administered. This indicates that water extracts of the rhizome of *Hedychium coronarium* do not have effect in reduction of blood glucose.

Example 11 Glucose Tolerance Test of Water-Ethanol Extract of Rhizome of *Hedychium Coronarium* in Normal Rats The test mice were fasted for 14 hours and then allowed to feed freely for one hour. Subsequently, 24 C57BL/6 mice were divided into four groups: a placebo group (6 mice administered with 10% Tween 20), a 0.5 g/kg HC group (6 mice administered with 0.5 g/kg water-ethanol extract of the rhizome of *Hedychium coronarium*), a 1.0 g/kg HC group (6 mice administered with 1.0 g/kg water-ethanol extract of the rhizome of *Hedychium coronarium*), and a 1.5 g/kg HC group (6 mice administered with 1.5 g/kg water-ethanol extract of the rhizome of *Hedychium coronarium*). After 30 minutes, the mice were intra-abdominally administered with glucose (1.5 g/kg) for the glucose tolerance test. Blood was drawn at 30-minute intervals for measurement of glucose (mg/dl). The results are shown in the table below.

| Group | Concentration of blood glucose (mg/dl) | | | |
|---|---|---|---|---|
| | 0 min | 30 mins | 60 mins | 90 mins |
| Placebo group | 109.7 +/− 5.5 | 228.5 +/− 16.1 | 127.3 +/− 3.6 | 109.2 +/− 5.5 |
| 0.5 g/kg HC group | 111.5 +/− 4.0 | 223 +/− 9.3 | 138 +/− 5.5 | 111 +/− 5.9 |
| 1 g/kg HC group | 111.8 +/− 3.8 | 216 +/− 20.1 | 134.7 +/− 6.5 | 105.2 +/− 3.5 |
| 1.5 g/kg HC group | 109.5 +/− 4.4 | 215 +/− 14.4 | 135.5 +/− 9.7 | 114 +/− 4.4 |

The data is expressed with mean +/− standard error (SEM). P values are calculated by t-test of Sigma Statistical Software wherein $p < 0.05$ is considered significant and marked with *; $p < 0.01$ is considered highly significant and marked with ; and $p \leq 0.001$ is considered very highly significant and marked with *.

The results show that compared with the control group, the groups administered with the water-ethanol extracts of the rhizome of *Hedychium coronarium* showed no difference in the concentrations of blood glucose at all time points after glucose was administered. This indicates that water-ethanol extracts of the rhizome of *Hedychium coronarium* do not have effect in reduction of blood glucose.

What is claimed is:

1. A method for lowering blood glucose, increasing insulin levels, reducing insulin resistance, and/or treating and/or preventing diabetes comprising administering an effective amount of leaves and pseudostems of an overground part of *Hedychium coronarium* Koenig or an extract thereof to a subject.

2. The method of claim 1, wherein the lowering of blood glucose does not occur in a fasting subject.

3. The method of claim 1, wherein the diabetes is type I or type II diabetes.

4. The method of claim 1, wherein the extract is obtainable from extracting the leaves and pseudostems of the overground part of *Hedychium coronarium* Koenig with a solvent.

5. The method of claim 4, wherein the leaves and pseudostems of the overground part of *Hedychium coronarium* Koenig is extracted with the solvent at a ratio of about 1:1 to about 1:100 (w/v (g/ml)).

6. The method of claim 5, wherein the solvent is selected from the group consisting of water, ethanol, ethanol/water mixture, methanol, butanol, iso-butanol, acetone, hexane, petroleum ether, and ethyl acetate.

7. The method of claim 6, wherein the solvent is selected from the group consisting of water, ethanol and an ethanol/water mixture.

8. The method of claim 7, wherein the water extract is prepared by washing the leaves and pseudostems of the overgroud part of *Hedychium coronarium*, grinding and drying (at about 60° C.) the plant sample to obtain a ground-dried plant sample, extracting the ground-dried plant sample with water at about 100° C. at a ratio of about 1:10 (w/v (g/ml)) for about 1 hour to obtain a crude product, filtrating and centrifuging the crude product to obtain a water extract, optionally re-extracting the remaining plant sample with water at about 100° C. at a ratio of about 1:10 (w/v (g/ml)) for about 1 hour to obtain a further crude product, filtrating and centrifuging the further crude product to obtain a further water extract, optionally combining the water extracts obtained from the previous two extractions to obtain a combined water extract, and concentrating the combined water extract to obtain a concentrated-combined water extract, and optionally preparing the concentrated-combined water extract at different dosages.

9. The method of claim 7, wherein the ethanol extract is prepared by washing the leaves and pseudostems of the overground part of *Hedychium coronarium*, grinding and drying (at about 60° C.) the plant sample to obtain a ground-dried plant sample, extracting the ground-dried plant sample with 95% ethanol at a ratio of about 1:10 (w/v (g/ml)) for about 16 hours to obtain a crude product, filtrating and centrifuging the crude product to obtain an ethanol extract, optionally re-extracting the remaining plant sample with ethanol at a ratio of about 1:10 (w/v (g/ml)) to obtain a further crude product, filtrating and centrifuging the further crude product to obtain a further ethanol extract, optionally combining the ethanol extracts obtained from the previous two extractions to obtain a combined ethanol extract, and concentrating the combined ethanol extract under reduced pressure at a temperature of about 40° C. to obtain a concentrated-combined ethanol extract, and optionally preparing the concentrated-combined ethanol extract at different dosages.

10. The method of claim 7, wherein the water-ethanol extract is prepared by washing the leaves and pseudostems of the overground part of *Hedychium coronarium*, grinding and drying (at about 60° C.) the plant sample a ground-dried plant sample, extracting the ground-dried plant sample with about 100° C. water at a ratio of about 1:10 (w/v (g/ml)) for about 1 hour to obtain a crude product, filtrating and centrifuging the crude product to obtain a water extract, optionally re-extracting the remaining plant sample with water at about 100° C. at a ratio of about 1:10 (w/v (g/ml)) for about 1 hour to obtain a further crude product, filtrating and centrifuging the further crude product to obtain a further water extract, optionally combining the water extracts obtained from the previous two extractions to obtain a combined water extract, diluting the combined water extract so that the v/w (ml/g) ratio of the diluted water extract to the ground-dried plant sample is about 1:1, adding ethanol to the diluted water extract so that the concentration of ethanol becomes about 70%, standing the ethanol solution for about 20 hours and then centrifuging and concentrating the resulting solution layer.

* * * * *